United States Patent [19]

Kidani et al.

[11] Patent Number: 4,797,485

[45] Date of Patent: Jan. 10, 1989

[54] PLATINUM-FLAVIN ANTI-TUMOR COMPLEXES

[75] Inventors: Yoshinori Kidani; Masahide Noji, both of Nagoya, Japan

[73] Assignee: Yoshinori Kidani, Japan

[21] Appl. No.: 99,301

[22] Filed: Sep. 17, 1987

[30] Foreign Application Priority Data

Sep. 19, 1986 [JP] Japan .................................. 61-219429

[51] Int. Cl.[4] ................ A61K 31/555; A61K 31/675; A61K 475/14; C07F 9/65
[52] U.S. Cl. .................................................... 544/225
[58] Field of Search ......................................... 544/225

[56] References Cited

PUBLICATIONS

Bowler, J. American Chemical Society 106, 6102 (1984).

Primary Examiner—Mark L. Berch
Attorney, Agent, or Firm—Larson and Taylor

[57] ABSTRACT

New platinum(II)-flavin complexes are now provided, which exhibit antitumor activities as shown by tests on mouse leukemia, L-1210 cells in mice. These novel platinum(II)-flavin complexes contain a 1,2-cyclohexanediamine, a 2-(aminomethyl)cyclohexylamine, an ethylenediamine or $NH_3$— groups as a ligand or ligands.

6 Claims, 5 Drawing Sheets

PLATINUM-FLAVIN ANTI-TUMOR COMPLEXES

SUMMARY OF THE INVENTION

This invention relates to new platinum(II)-flavin complexes which exhibit an antitumor activity as demonstrated by the test against mouse leukemia L-1210. The platinum(II)-flavin complexes of thi invention contain 1,2-cyclohexanediamine, 2-(aminomethyl)cyclohexylamine or ethylenediamine as a ligand.

BACKGROUND OF THE INVENTION

In recent years, a number of platinum(II) complexes, including well-known cisplatin, have been synthetized and have been reported to have antitumor activity. We, the present inventors, have synthesized some platinum-(II) complexes, as disclosed, for example, in Japanese Patent Application First Publn. (KOKAI) Nos. 31648/78, 35013/80, 130992/80, 103192/81, 156416/82, 16895/82, 21697/84, 34982/85, 34983/85, 97991/85, 109521/85 and 59289/87; Japanese Patent Application Second Publn. (KOKOKU) Nos. 29957/83, 34958/85 and 41077/85 as well as U.S. Pat. Nos. 4,169,846; 4,200,583; 4,256,652; 4,255,347; 4,551,524 and U.S. patent application Ser. No. 637,463 and European Patent Nos. 1126 and 8936, European Patent Appln. Nos. 83 303659.3 and 84 305304.2

We have also synthesized some organoplatinum (IV) complexes, as disclosed,for example, in Japanese Patent Application First Publication (KOKAI) Nos. 87295/85 and 109521/85; Japanese Patent Appln. No. 48625/86, as well as U.S. patent application Ser No. 020,893 and European Patent Appln. No. 87 420061.1.

Meanwhile, it is always demanded that new, antitumor platinum complexes having any more excellent properties than the known antitumor organoplatinum complexes are created and provided for uses in therapeutic treatment of tumors.

DETAILED DESCRIPTION OF THE INVENTION

Now, we, the present inventors, have succeeded in synthesizing new organo-platinum(II) compounds, more particularly, platinum(II)-flavin complexes of the formula (I) given below, and we have also found that thesc new dompounds, platinum(II)-flavin complexes now synthesized exhibit an antitumor activity as demonstrated by the test against mouse leukemia L-1210.

According to this invention, therefore, there is provided a new platinum(II)-flavin complex represented by the general formula (I)

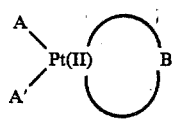
(I)

wherein A and A' taken together form a 1,2-cyclohexanediamine ligand of the formula:

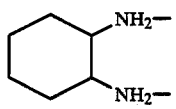

where the 1- and 2- amino groups have a configuration selected from cis-, trans-l- and trans-d-, relative to the cyclohexane ring; or A and A' taken together form a 2-(aminomethyl)cyclohexylamine ligand of the formula:

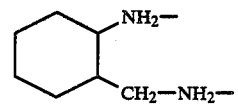

where the 1-amino group and 2-aminomethyl group have a configuration selected from cis-l-, cis-d-, trans-l- and trans-d-, or a mixture thereof, relative to the cyclohexane ring; or A and A' taken together form an ethylenediamine ligand of the formula:

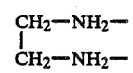

or A and A' each denote NH3—, and B denotes riboflavin or flavin-mononucleotide which coordinates the platinum(II) atom, or a nitrate of the platinum(II)-flavin complex of the formula (I).

With the platinum (II)-flavin complex of the formula (I) according to this invention where the moiety A

is the 1,2-cyclohexanediamine (abbreviated as dach), there are three stereo-isomers according to the following steric structures of the 1,2-cyclohexanediamine, namely 1,2-diaminocyclohexane moiety.

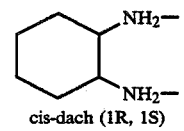
cis-dach (1R, 1S)

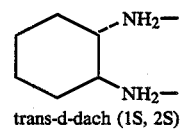
trans-d-dach (1S, 2S)

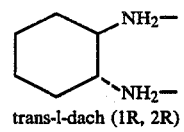
trans-l-dach (1R, 2R)

With the platinum(II)-flavin complex of the formula (I) according to this invention where the moiety

is the 2-(aminomethyl)cyclohexylamine (abbreviated as amcha), there are four stereo-isomers according to the following steric structures of the 2-(aminomethyl)cyclohexylamine, namely 1-amino-2-aminomethylcyclohexane moiety:

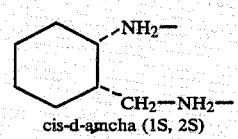
cis-d-amcha (1S, 2S)

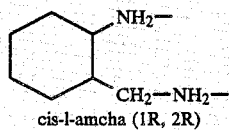
cis-l-amcha (1R, 2R)

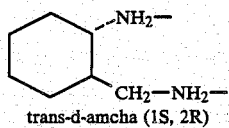
trans-d-amcha (1S, 2R)

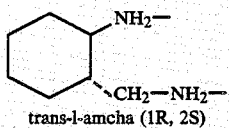
trans-l-amcha (1R, 2S)

The platinum (II)-flavin complex of the formula (I) according to this invention, therefore, includes some different stereo-isomers as shown above, depending on the configuration of the 1,2-cyclohexanediamine or 2-(aminomethyl) cyclohexylamine which forms a ligand to the platinum atom.

The platinum(II)-flavin complex of the general formula (I) according to this invention may be prepared according to the process wherein such a dinitrato-platinum (II) complex, in which a desired particular ligand such as the 1,2-cyclohexanediamine (namely, dach) or the 2-(aminomethyl)cyclohexylamine (namely, amcha) ligand has coordinated the platinum(II) atom and which is represented by the formula:

where A and A' are as defined above, is reacted with riboflavin (namely, vitamin B₂) or riboflavin-mononucleotide which will give the leaving group, with the reaction being conducted in a suitable solvent. The starting material, namely the dinitrato-platinum (II) complex of formula (II) may be prepared according to a known method, for example, the method disclosed in Japanese Patent Second Publication (KOKOKU) No. 29957/83 or U.S. Pat. Nos. 4,256,652; 4,255,347 and 4,551,524.

The new platinum (II)-flavin complex according to this invention exhibits anti-tumor activity against experimental tumors in mouse, such as L-1210, P-388 and S-180A (ascites tumor), and therefore is useful in chemotherapeutics of tumors. The new platinum (II)-flavin complex of this invention can be administered orally, intramuscularly or intravenously. It can be formulated into capsules, powders, pellets or injections.

Suitable dosage of the platinum(II)-flavin complex of this invention is about 1 to 400 mg/kg/day.

The production of the novel platinum(II)-flavin complex of the formula (I) according to this invention is now illustrated with reference to the following Examples. The data of elementary analysis and yield of the platinum(II)-flavin complex as produced in these Examples are tabulated in Table 1 hereinafter. Compound Nos. given in Table 1 are corresponding to the Example Nos. in which the platinum complex indicated was prepared.

EXAMPLE 1

Preparation of riboflavin-(trans-l-dach)platinum (II) complex nitrate, namely platinum(riboflavinato) (trans-l-dach).NO₃ of the formula

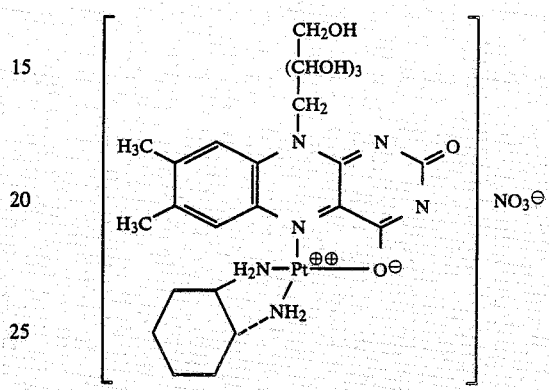

Di-nitrato-(trans-l-dach)platinum(II) complex, namely (NO₃)₂(trans-l-dach)platinum(II) complex, (0.437 g, 1 mmol.) represented by the formula

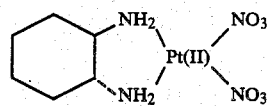

was dissolved in water (30 ml) under heating to give an aqueous solution. Riboflavin (0.377 g, 1 mmol.) was added in another volume of water (100 ml) under stirring and heating so that riboflavin was partially dissolved in the hot water, to give a yellowish aqueous suspension in which a part of riboflavin was dissolved and another part of riboflavin was dispersed as solid fine particles. To this yellowish suspension was added in small portions the aqueous solution of (NO₃)₂(trans-l-dach)platinum(II) complex as prepared above, while the resulting liquid mixture was warmed on a water bath under stirring and heating. The yellowish liquid mixture as initially formed was gradually discolored to give a reaction solution of blood red color, as the dissolution took place.

The resulting red-colored solution was further kept on a water bath at a temperature 50° to 60° C. for about 1 hour and then allowed to stand at room tmperature for 2 hours.

The reddish reaction solution was filtered to remove completely therefrom the solid particles of riboflavin which were remaining undissolved. The reddish filtrate obtained was concentrated to dryness by means of a flash evaporator. The resulting solid residue was washed with hot ethanol, and the remaining solid residue was subsequently washed with hot acetone and was then recovered by filtration, to afford the titled platinum(II) complex as a reddish powder. This complex was readily soluble in water, and soluble in ethanol.

EXAMPLE 2

Preparation of riboflavin-(trans-d-dach)platinum(II) complex nitrate.

Dinitrato(trans-d-dach)platinum(II) (0.437 g, 1 mmol.) was employed as a starting material, in place of the dinitrato(trans-l-dach)platinum(II) which was used in Example 1 above, and it was reacted with riboflavin and the reaction mixture was then processed in the same manner as in Example 1 above, to afford the titled platinum(II) complex.

EXAMPLE 3

Preparation of riboflavin-(cis-dach)platinum(II) complex nitrate.

Dinitrato(cis-dach)platinum(II) complex (0.437 g, 1 mmol.) was employed as a starting material in place of the $(NO_3)_2$(trans-l-dach)platinum(II) complex which was used in Example 1 above. It was reacted with riboflavin and the reaction mixture was then processed in the same manner as in Example 1, to afford the titled platinum(II) complex.

EXAMPLE 4

Preparation of riboflavinmononucleotide(trans-l-dach)platinum(II) complex of the formula:

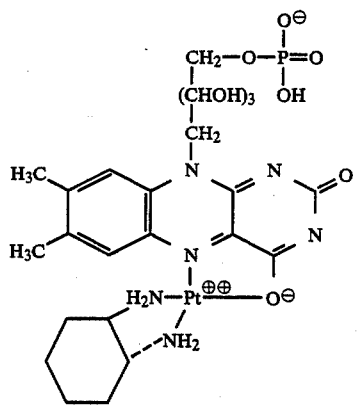

Dinitrato-(trans-l-dach)platinum(II) complex (0.437 g, 1 mmol.) was dissolved in water (30 ml) under heating to give an aqueous solution. Riboflavin-mononucleotide (0.478 g, 1 mmol.) of the formula

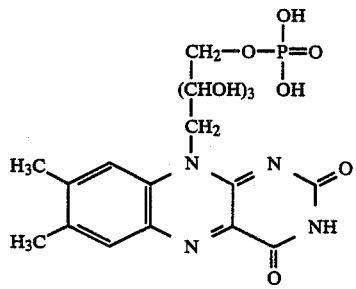

was dissolved in water (40 ml) under stirring and heating, to obtain a yellowish solution. To the resulting yellowish solution was added in small portions the aqueous solution of the dinitrato (trans-l-dach)platinum-(II) complex as prepared above, and the mixture as obtained was then kept on a water bath for about 1 hour under heating. A red-colored reaction solution was thus obtained. The solution so obtained was concentrated to dryness by means of flash evaporator. The resulting solid residue was washed with hot ethanol, followed by filtration, to afford the titled platinum(II) complex as a reddish powdery product. This reddish powdery product is readily soluble in water but insoluble in ethanol.

EXAMPLE 5

Preparation of riboflavinmononucleotide(trans-d-dach)platinum(II) complex.

Dinitrato (trans-d-dach)platinum(II) complex (0.478 g, 1 mmol.) was employed as a starting material in place of the $(NO_3)_2$(trans-l-dach)platinum(II) complex which was used in Example 4 above. It was reacted with riboflavin-mononucleotide and the reaction mixture was processed in the same manner as in Example 4, to afford the titled platinum(II) complex.

EXAMPLE 6

Preparation of riboflavinmononucleotide(cis-dach) platinum(II) complex.

Dinitrato(cis-dach)platinum(II) complex (0.478 g, 1 mmol.) was employed as a starting material in place the $(NO_3)_2$(trans-l-dach)platinum(II) complex which was used in Example 4 above. It was reacted with riboflavinmononucleotide and the reaction mixture was processed in the same manner as in Example 4, to afford the titled platinum(II) complex.

EXAMPLE 7

Preparation of riboflavin-$(NH_3)_2$-platinum(II) complex nitrate.

Cis-$(NH_2(NO_3)_2$platinum(II) complex (0.353 g, 1 mmol.) was dissolved in water (20 ml) under heating to give an aqueous solution. Riboflavin (0.377 g, 1 mmol.) was added into water (100 ml) under heating. Riboflavin was partially dissolved and suspended in hot water to afford a yellowish aqueous suspension of riboflavin. To the resulting yellowish suspension of riboflavin was added in small portions the aqueous solution of the cis-$(NH_3)_2(NO_3)_2$ platinum(II) complex prepared as above. The mixture obtained was kept on a water bath under stirring and heating, so that a reddish reaction solution was obtained. After standing on a water bath under heating for about one hour, the reaction solution was filtered. The filtrate obtained was concentrated to dryness by means of flash evaporator. The resulting solid residue was washed with hot ethanol, followed by filtration to recover the insoluble solid product. The solid product thus recovered was washed with hot acetone, followed by filtration, to afford the titled platinum(II) complex as a reddish powder. This complex is readily soluble in water but insoluble in ethanol and acetone.

EXAMPLE 8

Preparation of riboflavin-(ethylenediamine)platinum (II) complex nitrate.

Dinitrato(ethylenediamine)platinum(II) complex (0.379 g, 1 mmol.) was dissolved in water (20 ml) under heating to give an aqueous solution. Riboflavin (0.377 g, 1 mmol.) was added into water (100 ml) under heating, so that riboflavin was partially dissolved and suspended in the hot water to give a yellowish aqueous suspension of riboflavin. To the resulting yellowish suspension of the riboflavin was added in small portions the aqueous solution of the $(NO_3)_2$ (ethylenediamine) platinum(II) complex prepared as above. The mixture obtained was kept on a water bath under stirring and heating, so that a reddish reaction solution was obtained. After standing on a water bath under heating for about one hour, the reaction solution was filtered. The filtrate obtained was concentrated to dryness by means of flash evaporator. The resulting solid residue was washed with hot ethanol, followed by filtration to recover the solid product. The solid product thus recovered was washed with hot acetone, followed by filtration, to afford the titled platinum(II) complex as a reddish powder. This complex was readily soluble in water but insoluble in ethanol and acetone.

EXAMPLE 9

Preparation of riboflavin-(cis-dl-amcha)platinum (II) complex nitrate of the formula:

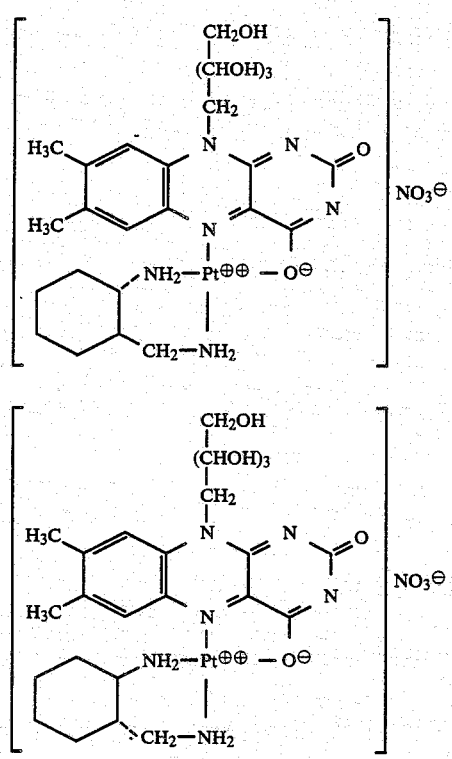

Dinitrato(cis-dl-amcha)platinum(II) complex (0.447 g, 1 mmol.) was dissolved in water (20 ml) under heating to give an aqueous solution. Riboflavin (0.377 g, 1 mmol) was added into water (100 ml) under stirring and heating, so that riboflavin was partially dissolved and suspended in the hot water, to yield a yellowish aqueous suspension of riboflavin. To the resulting yellowish suspension of riboflavin was added the aqueous solution of the dinitrato(cis-dl-amcha)platinum(II) complex prepared as above. The mixture as obtained was kept on a water bath under stirring and heating, so that a reddish reaction solution was formed. After standing on a water bath for about one hour under heating, the reaction solution was filtered. The filtrate obtained was concentrated to dryness by means of flash evaporator. The resulting solid residue was washed with hot ethanol, and the remaining solid residue was subsequently washed with hot acetone and it was then recovered by filtration to afford the solid product of the titled platinum(II) complex. This complex was readily soluble in water and ethanol but insoluble in acetone.

EXAMPLE 10

Preparation of riboflavin-(trans-dl-amcha)platinum (II) complex nitrate.

Dinitrato(trans-dl-amcha)platinum(II) complex (0.377 g, 1 mmol) was employed as a starting material in place of the dinitrato(cis-dl-amcha)platinum(II) which was used in Example 9 above. It was reacted with riboflavin and the reaction mixture was processed in the same manner as in Example 9, to afford the titled platinum(II) complex.

EXAMPLE 11

Preparation of riboflavinmononucleotide-$(NH_3)_2$ platinum(II) complex.

Cis-$(NO_3)_2(NH_3)_2$platinum(II) complex (0.353 g, 1 mmol.) was dissolved in water (20 ml) under heating. Riboflavin-mononucleotide (0.473 g, 1 mmol.) was dissolved in water (40 ml) under heating, to give a yellowish solution of the mononucleotide. To the resulting yellowish solution of riboflavin-mononucleotide was added the aqueous solution of the cis-$(NO_3)_2(NH_3)_2$ platinum(II) complex prepared as above. The liquid mixture obtained was heated on a water bath to afford a reddish reaction solution.

After standing on a water bath for about one hour, the reddish reaction solution was concentrated to dryness by means of flash evaporator. The resulting solid residue was washed with hot ethanol, and filtered out to recover the solid product. The titled platinum(II) complex was thus obtained as a reddish powder, which was readily soluble in water but insoluble in alcohols.

EXAMPLE 12

Preparation of riboflavinmononucleotide(ethylenediamine)platinum(II) complex of the formula:

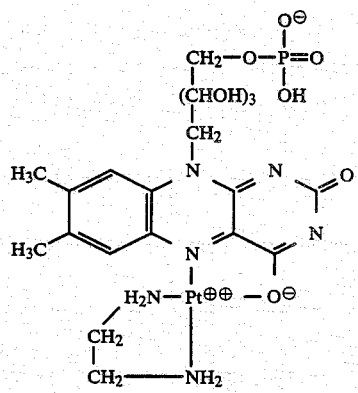

Dinitrato(ethylenediamine)platinum(II) complex (0.379 g, 1 mmol.) was dissolved in water (20 ml) under heating to give an aqueous solution. Riboflavin-mononucleotide (0.473 g, 1 mmol.) was dissolved in water (40 ml) under heating, to give a yellowish solution. To the resulting yellowish solution of riboflavin-mononucleotide was added the aqueous solution of the dinitrato(ethylenediamine)platinum(II) complex prepared as above. The resulting liquid mixture was heated on a water bath to give a reddish reaction solution. After standing on a water bath under heating for about one hour, the reddish reaction solution was concentrated to dryness by means of flash evaporator. The resulting solid residue was washed with hot ethanol, and recovered by filtration. The titled platinum(II) complex was thus obtained as a reddish powder, which was readily soluble in water but insoluble in ethanol.

EXAMPLE 13

Preparation of riboflavinmononuleotide-(cis-dl-amcha) platinum(II) complex.

Dinitrato(cis-dl-amcha)platinum(II) complex (0.447 g, 1 mmol.) was dissolved in water (20 ml) under heating to give an aqueous solution. Riboflavin-mononucleotide (0.473 g, 1 mmol.) was dissolved in water (40 ml), to yield a yellowish solution. To the resulting yellowish solution of riboflavin-mononucleotide was added in small portions the aqueous solution of the dinitrato(cis-dl-amcha)platinum(II), while the resulting liquid mixture was heated on a water bath. Thus, a reddish reaction solution was finally formed. The reaction solution was heated on a water bath for about one hour, and thereafter the reaction solution was concentrated to dryness by means of flash evaporator. The resulting solid residue was washed with hot ethanol and then recovered by filtration. Thus, the titled platinum-(II) complex was obtained as a reddish powder, which was readily soluble in water but insoluble in ethanol.

EXAMPLE 14

Preparation of riboflavinmononucleotide-(trans-dl-amcha)platinum(II) complex of the formula:

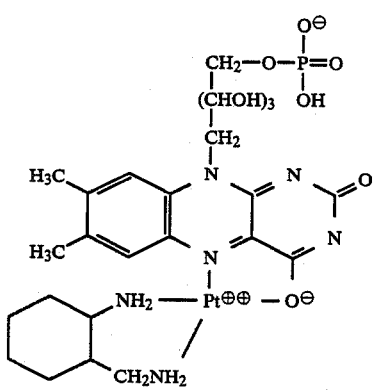

Dinitrato(trans-dl-amcha)platinum(II) complex (0.447 g, 1 mmol.) was employed as a starting material in place of the dinitrato(cis-dl-amcha)platinum(II) which was used in Example 13 above. It was reacted with riboflavin-mononucleotide nad the reaction mixutre was processed in the same manner as in Example 13, to afford the titled platinum (II) complex.

The elementary analysis values and the yields of the respective platinum(II)-riboflavin complexes as obtained in the above Examples 1 to 14 according to this invention are summarized in Table 1 below.

TABLE 1

| Compound No. (Example No.) | Calculated value (%) | | | Found value (%) | | | Yield (%) |
|---|---|---|---|---|---|---|---|
| | H | O | N | H | O | N | |
| 1 | | | | 4.20 | 35.10 | 13.46 | 85 |
| 2 | 4.42 | 36.99 | 13.13 | 4.22 | 35.37 | 13.63 | 85 |
| 3 | | | | 4.13 | 36.04 | 13.67 | 75 |
| 4 | | | | 4.08 | 35.44 | 10.83 | 85 |
| 5 | 4.44 | 36.07 | 10.98 | 4.30 | 36.10 | 11.03 | 85 |
| 6 | | | | 4.30 | 35.39 | 10.40 | 85 |
| 7 | 3.89 | 30.58 | 14.69 | 3.57 | 23.74 | 15.59 | 90 |

TABLE 1-continued

| Compound No. (Example No.) | Calculated value (%) | | | Found value (%) | | | Yield (%) |
|---|---|---|---|---|---|---|---|
| | H | O | N | H | O | N | |
| 8 | 4.04 | 32.90 | 14.14 | 3.97 | 31.64 | 13.88 | 85 |
| 9 | 4.73 | 37.84 | 12.87 | 4.37 | 37.10 | 12.71 | 85 |
| 10 | | | | 4.66 | 37.54 | 12.70 | 85 |
| 11 | 3.86 | 31.31 | 12.89 | 3.77 | 30.22 | 12.64 | 80 |
| 12 | 4.07 | 32.07 | 11.79 | 3.03 | 23.22 | 12.63 | 80 |
| 13 | 4.62 | 36.97 | 10.78 | 4.47 | 36.50 | 10.81 | 75 |
| 14 | | | | 4.39 | 36.27 | 10.43 | 75 |

BRIEF DESCRIPTION OF THE DRAWINGS

With reference to the attached drawings.

Experiment 1

Figure 1:
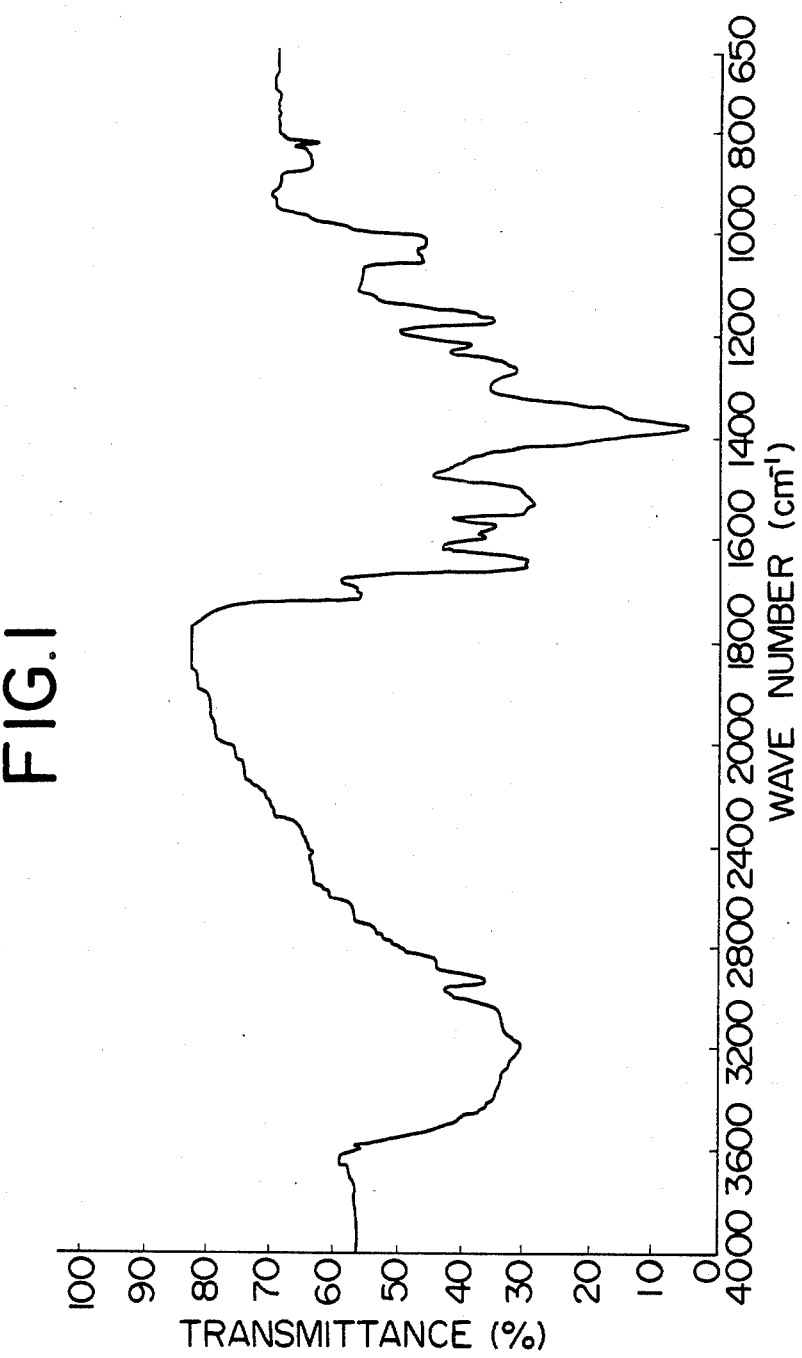
FIG. 1 shows a curve of the infrared absorption spectrum (KBr) of the riboflavin-(trans-l-dach)platinum (II) complex nitrate as prepared in the Example 1 of this invention.
Figure 2:
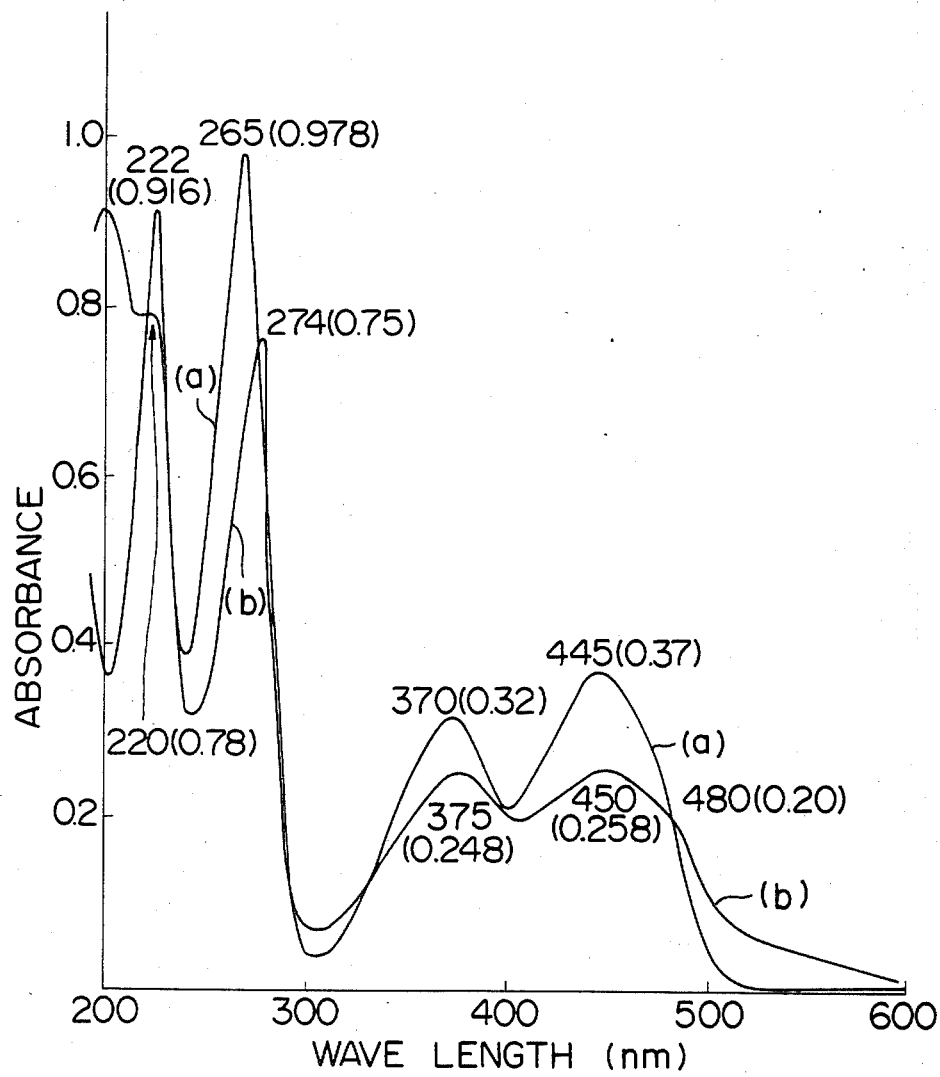
FIG. 2 shows curves of the absorption spectra in the ultraviolet and visible wave length regions of riboflavin (Curve-a) and the riboflavin-(trans-l-dach)platinum(II) complex nitrate (Curve-b) of the Example 1 of this invention, as measured at the concentration of $5 \times 10^{-5}$ mol./l. Values of the wave length at the absorption peaks and the values of their absorbance (given in parenthesis) in the spectra are also indicated in FIG. 2.
Figure 3:
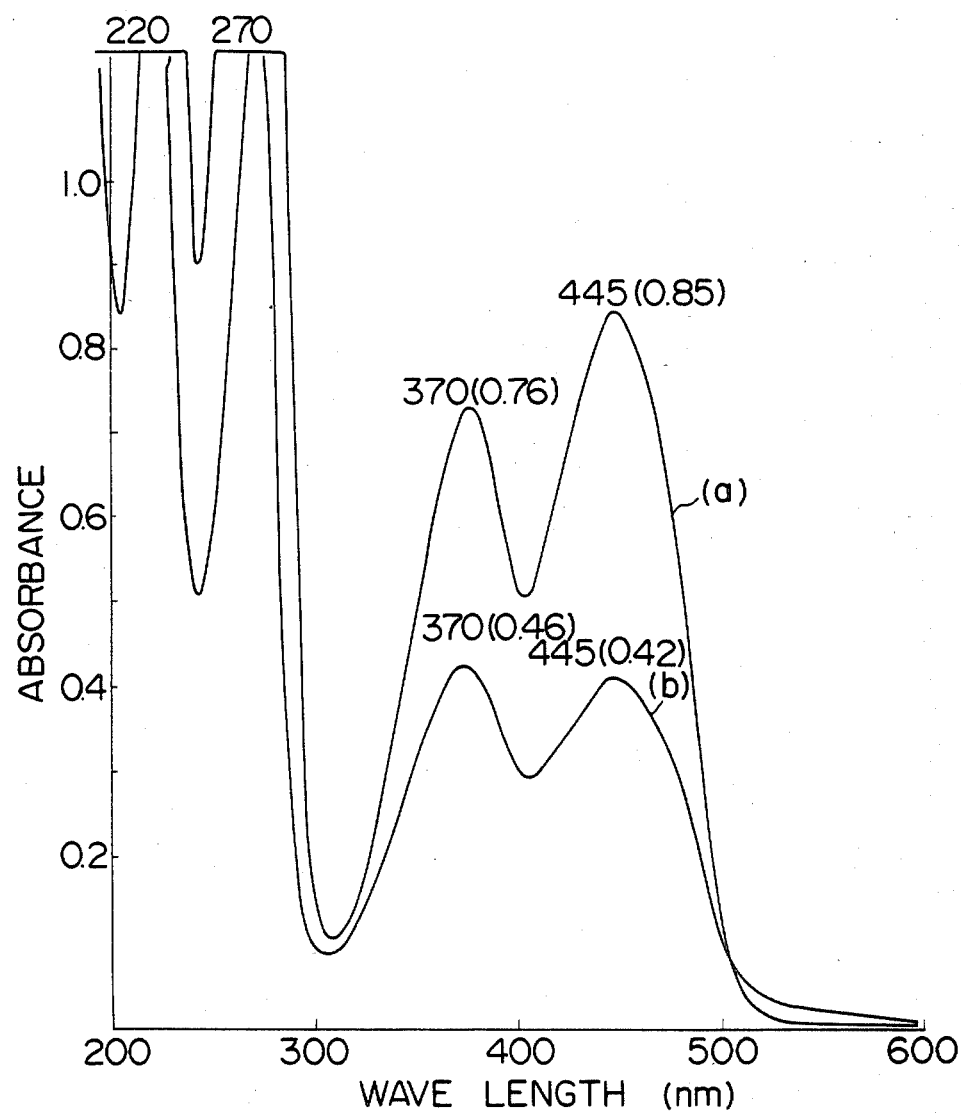
FIG. 3 shows curves of the absorption spectra in the ultraviolet and visible wave length regions of ribolavin-mononucleotide (trans-l-dach)platinum(II) complex nitrate (Curve-b) as prepared in the Example 4 of to this invention, as measured at the concentration of $10^{-4}$ mol./l of riboflavinmononucleotide and at the concentration of $5 \times 10^{-5}$ mol./l of the riboflavinmononucleotide-(trans-l-dach)platinum (II) complex nitrate. Values of the wave length at the absorption peaks and the values of their absorbance (given in parenthesis) in these spectra are also indicated in FIG. 3.
Figure 4:
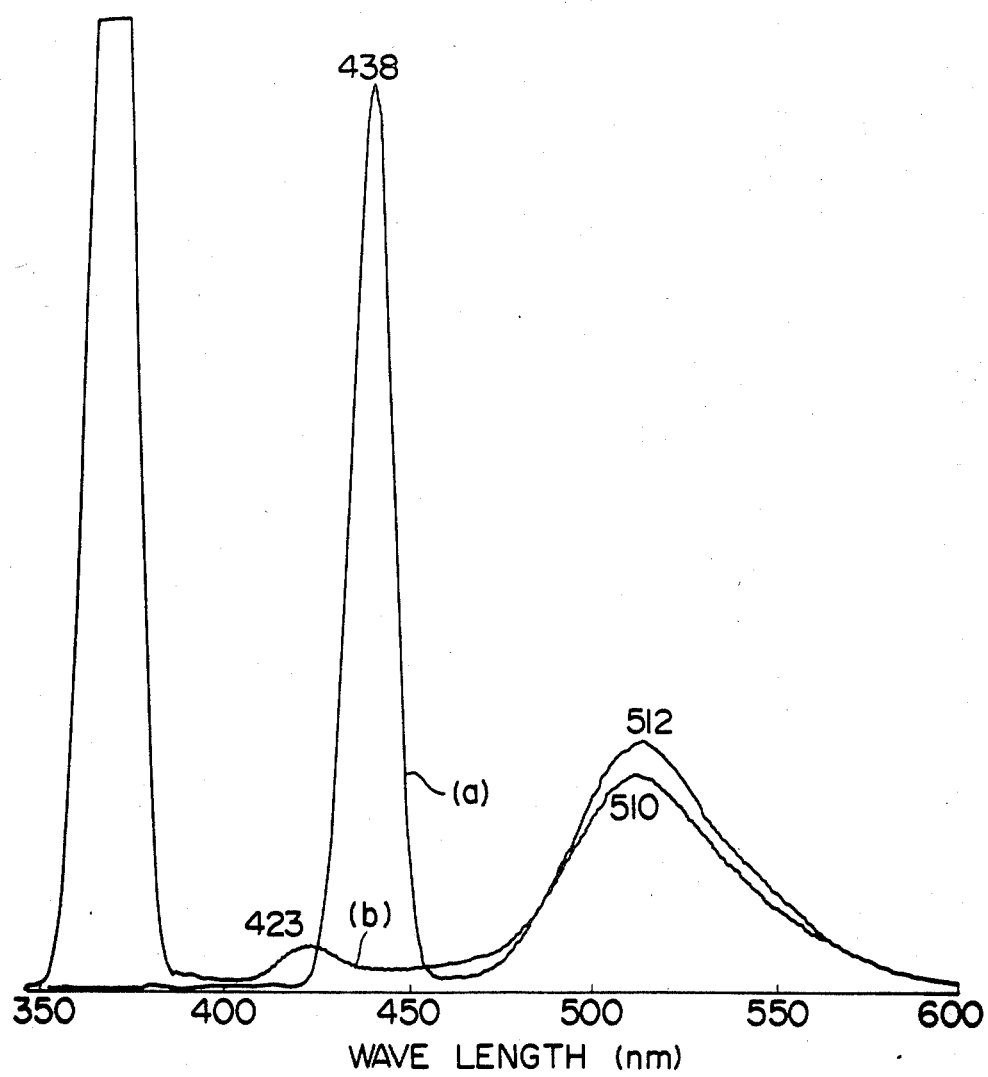
FIG. 4 shows a curve of the fluorescence spectrum of riboflavin as excited at 440 nm (Curve-a) or at 370 nm (Curve-b), and as measured at the concentration of $10^{-7}$ mol./l of riboflavin.
Figure 5:
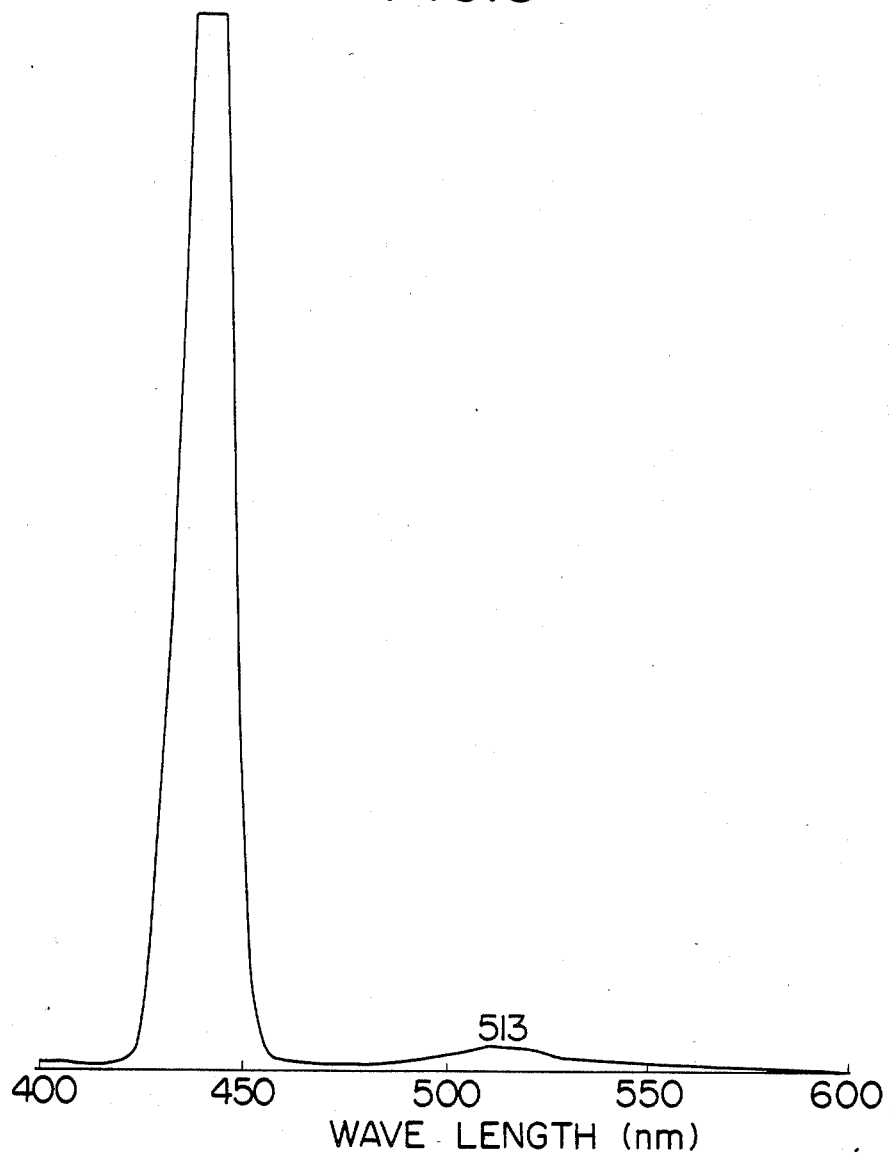
FIG. 5 shows a curve of the fluorescence spectrum of the riboflavin-(trans-l-dach)platinum(II) complex nitrate of the Example 1, as excited at 440 nm and measured at the concentration of $10^{-7}$ mol./l of said complex.

Anti-tumor activity of the platinum(II)-flavin complex of this invention in mice against Leukemia L-1210 is now estimated.

To test the anti-tumor activity of the platinum (II)-flavin complexes according to this invention, $10^5$ cells/mouse of Leukemia L-1210 were transplanted by intraperitoneal injection to groups of $CDF_1$ mice (6 mice in each group)on day 0. On the next day after the transplantation and days 5 and 9 after the transplantation of Leukemia L-1210 cells, the platinum(II)-flavin complex under test was administered by intraperitoneal injection to the test mice. The antitumor activity of the test platinum(II)-flavin complex was evaluated by means of the ratio (%) of prolongation of mean survival days of the treated mice, in term of the values of T/C %, namely the value of 100 times the mean survival period of the groups of mice treated with the test platinum(II)-flavin complex, divided by the mean survival period of the comparative groups of mice which were not treated with the test platinum(II)-flavin complex. The test results are as shown in Table 2 below. In Table 2, the T/C (%) values of higher than 125% means that the tested platinum (II)-flavin complex has a substantial anti-tumor activity.

In Table 2, the numerical figures given in the parenthesis denotes the number of the mice as entirely cured in each group of mice treated, on the 30 day observation. The term "T" denotes that the incurred decrease in body weight of the treated mice within 5 days of the test exceeded the lowest limit value (−4 g) for judgement of the toxic effects of the test compound. The test results shown in Table 2 demonstrates that the platinum(II)-flavin complexes of this invention have a significant anti-tumor activity.

TABLE 2

| Compound No. of platinum (II) complex | Ratio (%) of prolongation of mean survival period (T/C, %) Dose (mg/kg) | | | | | | | | | |
|---|---|---|---|---|---|---|---|---|---|---|
| | 400 | 200 | 100 | 50 | 25 | 12.5 | 6.25 | 3.12 | 1.56 | 0.78 | 0.39 |
| 1 | | | | | 192(1) | 167 | 129 | | | | |
| 2 | | | | | 177 | 145 | 124 | | | | |
| 3 | 0 | 0 | 0 | 165 | 115 | 105 | 100 | | | | |
| 4 | | | T170(1) | 326(4) | 253(1) | 185 | 124 | 125 | 115 | | |
| 5 | | | | 161(1) | 121 | 109 | | | | | |
| 6 | | | | 114 | 117 | 105 | | | | | |
| 7 | | | 139 | 136 | 146 | 115 | 106 | | | | |
| 8 | | | | 116 | 109 | 101 | | | | | |
| 9 | | | | 133(1) | 196 | 169(1) | | | | | |
| 10 | | | | 89 | 192 | 125 | | | | | |
| 11 | | | | | 96 | 102 | 96 | | | | |
| 12 | | | | 113 | 104 | 103 | | | | | |
| 13 | | | | 134 | 112 | 119 | | | | | |
| 14 | | | | 146 | 179 | 130 | | | | | |
| Comparative compound* | | | | | 100 | 231(4) | 335(3) | 231(1) | 189 | 144 | 134 |

*Comparative compound: (NO₃)₂(trans-1-dach)platinum(II) complex

What we claim is:

1. An anti-tumor platinum(II)-flavin complex represented by the general formula (I)

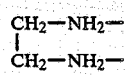

wherein A and A' taken together form a 1,2-cyclohexanediamine ligand of the formula:

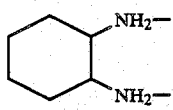

where the 1- and 2-amino groups have a configuration selected from cis-, trans-l- and trans-d-, relative to the cyclohexane ring; or A and A' taken together form a 2-(aminomethyl)cyclohexylamine ligand of the formula:

where the 1-amino group and 2-aminomethyl group have a configuration selected from cis-l-, cis-d-, trans-l and trans-d-, or a mixture thereof, relative to the cyclohexane ring; or A and A' taken together form an ethylenediamine ligand of the formula:

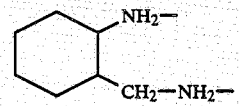

A and A' each denote NH₃-, and B denotes riboflavin or riboflavin-mononucleotide which coordinates the platinum atom, or a nitrate of the platinum(II)-flavin complex of the formula (I).

2. A platinum(II)-flavin complex of claim 1 in which A and A' taken together form a ligand selected from cis-1,2-cyclohexanediamine, trans-d-1,2-cyclohexandiamine, and trans-l-1,2-cyclohexanediamine; and B is riboflavin or riboflavin-mononucleotide.

3. A platinum(II)-flavin complex of claim 1 in which A and A' taken together form a ligand selected from cis-dl-2-(aminomethyl)cyclohexylamine and trans-dl-2-(aminomethyl)cyclohexylamine; and B is riboflavin or riboflavin-mononucleotide.

4. Riboflavin-(trans-l-1,2-cyclohexanediamine) platinum(II) complex nitrate of the formula:

5. Riboflavinmononucleotide-(trans-l-1,2-cyclohexanediamine)platinum(II) complex of the formula:
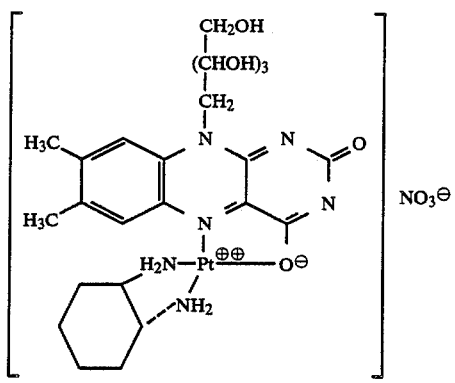
6. Riboflavin-(cis- or trans-dl-2-(aminomethyl) cyclohexylamine)platinum(II) complex nitrate of the formula:
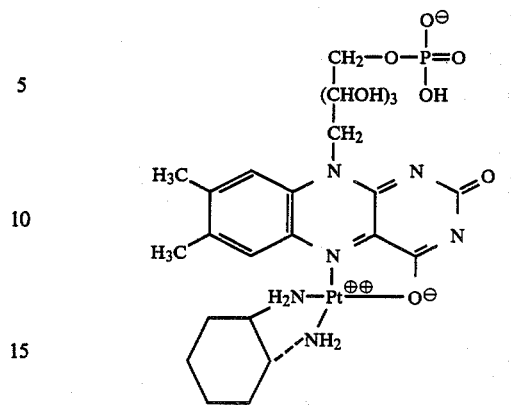
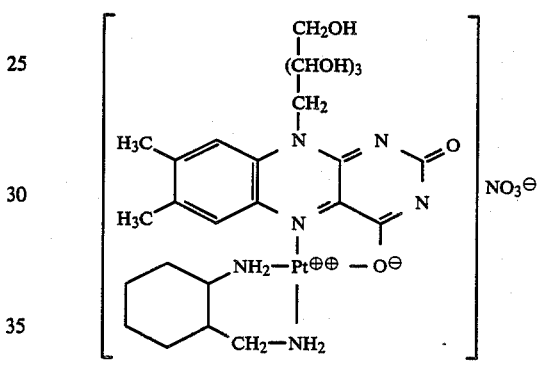
* * * * *